(12) United States Patent
Koh et al.

(10) Patent No.: US 11,638,782 B2
(45) Date of Patent: May 2, 2023

(54) SEALANT SYRINGE ASSEMBLY

(71) Applicant: SAMYANG HOLDINGS CORPORATION, Seoul (KR)

(72) Inventors: Young Joo Koh, Daejeon (KR); Hyung Hwan Kim, Seongnam-si (KR); Jung Ha Park, Seoul (KR)

(73) Assignee: SAMYANG HOLDINGS CORPORATION, Seoul (KR)

( * ) Notice: Subject to any disclaimer, the term of this patent is extended or adjusted under 35 U.S.C. 154(b) by 553 days.

(21) Appl. No.: 16/636,708

(22) PCT Filed: Aug. 7, 2018

(86) PCT No.: PCT/KR2018/008991
§ 371 (c)(1),
(2) Date: Feb. 5, 2020

(87) PCT Pub. No.: WO2019/050169
PCT Pub. Date: Mar. 14, 2019

(65) Prior Publication Data
US 2020/0238009 A1 Jul. 30, 2020

(30) Foreign Application Priority Data

Sep. 8, 2017 (KR) .................. 10-2017-0114871
Sep. 8, 2017 (KR) .................. 10-2017-0114872

(51) Int. Cl.
*A61M 5/19* (2006.01)
*A61L 24/04* (2006.01)
(Continued)

(52) U.S. Cl.
CPC ............. *A61M 5/19* (2013.01); *A61L 24/043* (2013.01); *A61L 24/104* (2013.01);
(Continued)

(58) Field of Classification Search
CPC ...... A61M 5/19; A61M 3/005; A61M 5/1408; A61M 5/1409; A61M 5/2448;
(Continued)

(56) References Cited

U.S. PATENT DOCUMENTS 4,735,616 A * 4/1988 Eibl .................. A61B 17/00491
604/191
4,874,368 A * 10/1989 Miller .............. A61B 17/00491
604/82
(Continued)

FOREIGN PATENT DOCUMENTS

| JP | 2011-527607 A | 11/2011 |
|---|---|---|
| JP | 2012-110514 A | 6/2012 |

(Continued)

OTHER PUBLICATIONS

International Search Report, issued in PCT/KR2018/008991, dated Nov. 7, 2018.

*Primary Examiner* — Nilay J Shah
(74) *Attorney, Agent, or Firm* — Birch, Stewart, Kolasch & Birch, LLP

(57) ABSTRACT

A sealant syringe assembly includes a first syringe including a plurality of chambers and discharging a first solution which is a mixture of a buffer solution and compound powder; a reaction solution syringe including at least one chamber and discharging a reaction solution capable of reacting with the first solution; and a connector for connecting the first syringe and the reaction solution syringe to mix and discharge the first solution and the reaction solution. The first syringe includes three packing members provided inside the first syringe; a passage provided in the inner circumferential surface of the first syringe; and a plunger for providing a pressure to one of the packing members.

15 Claims, 6 Drawing Sheets

(51) Int. Cl.
*A61L 24/10* (2006.01)
*A61M 5/24* (2006.01)
*A61M 3/00* (2006.01)

(52) U.S. Cl.
CPC ........... *A61L 24/108* (2013.01); *A61M 3/005* (2013.01); *A61M 5/2448* (2013.01); *A61L 24/04* (2013.01)

(58) Field of Classification Search
CPC .......... A61M 2005/31598; A61L 24/02; A61L 24/04; A61L 24/08; A61L 24/104; A61L 24/108
See application file for complete search history.

(56) References Cited

U.S. PATENT DOCUMENTS

| | | | |
|---|---|---|---|
| 5,290,259 A * | 3/1994 | Fischer | A61M 5/19 222/137 |
| 5,599,312 A * | 2/1997 | Higashikawa | A61M 5/284 604/218 |
| 5,720,731 A | 2/1998 | Aramata et al. | |
| 6,936,033 B2 | 8/2005 | McIntosh et al. | |
| 8,376,989 B2 | 2/2013 | Rissman et al. | |
| 2001/0003126 A1 * | 6/2001 | Rhee | A61L 24/043 525/425 |
| 2003/0111552 A1 * | 6/2003 | Vedrine | A61M 5/284 239/533.1 |
| 2002/0233067 | 12/2003 | McIntosh et al. | |
| 2003/0233067 A1 * | 12/2003 | McIntosh | A61B 17/00491 604/82 |
| 2009/0209919 A1 | 8/2009 | Sakurai et al. | |
| 2010/0010473 A1 | 1/2010 | D'Alessic et al. | |
| 2010/0198255 A1 | 8/2010 | Ifuku et al. | |
| 2010/0233246 A1 * | 9/2010 | Sehl | C08L 71/02 424/443 |
| 2011/0021982 A1 * | 1/2011 | Keller | B05C 17/00553 604/82 |
| 2012/0095394 A1 | 4/2012 | Kakiuchi et al. | |
| 2014/0316341 A1 | 10/2014 | Holtwick et al. | |
| 2015/0057638 A1 | 2/2015 | Davidian et al. | |
| 2017/0050002 A1 | 2/2017 | Steffen | |

FOREIGN PATENT DOCUMENTS

| | | |
|---|---|---|
| JP | 2014-533535 A | 12/2014 |
| KR | 20-0468340 Y1 | 8/2013 |
| WO | WO 2008/153059 A1 | 12/2008 |

* cited by examiner

[FIG. 1]
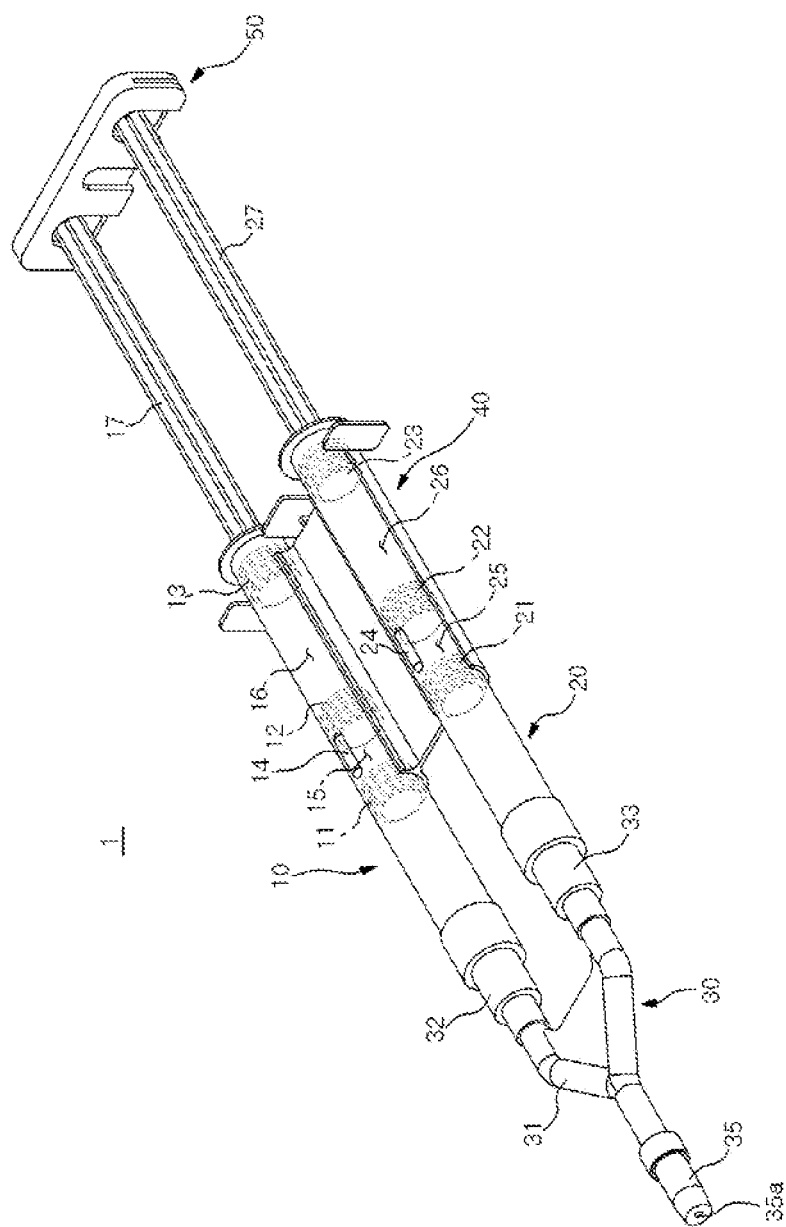

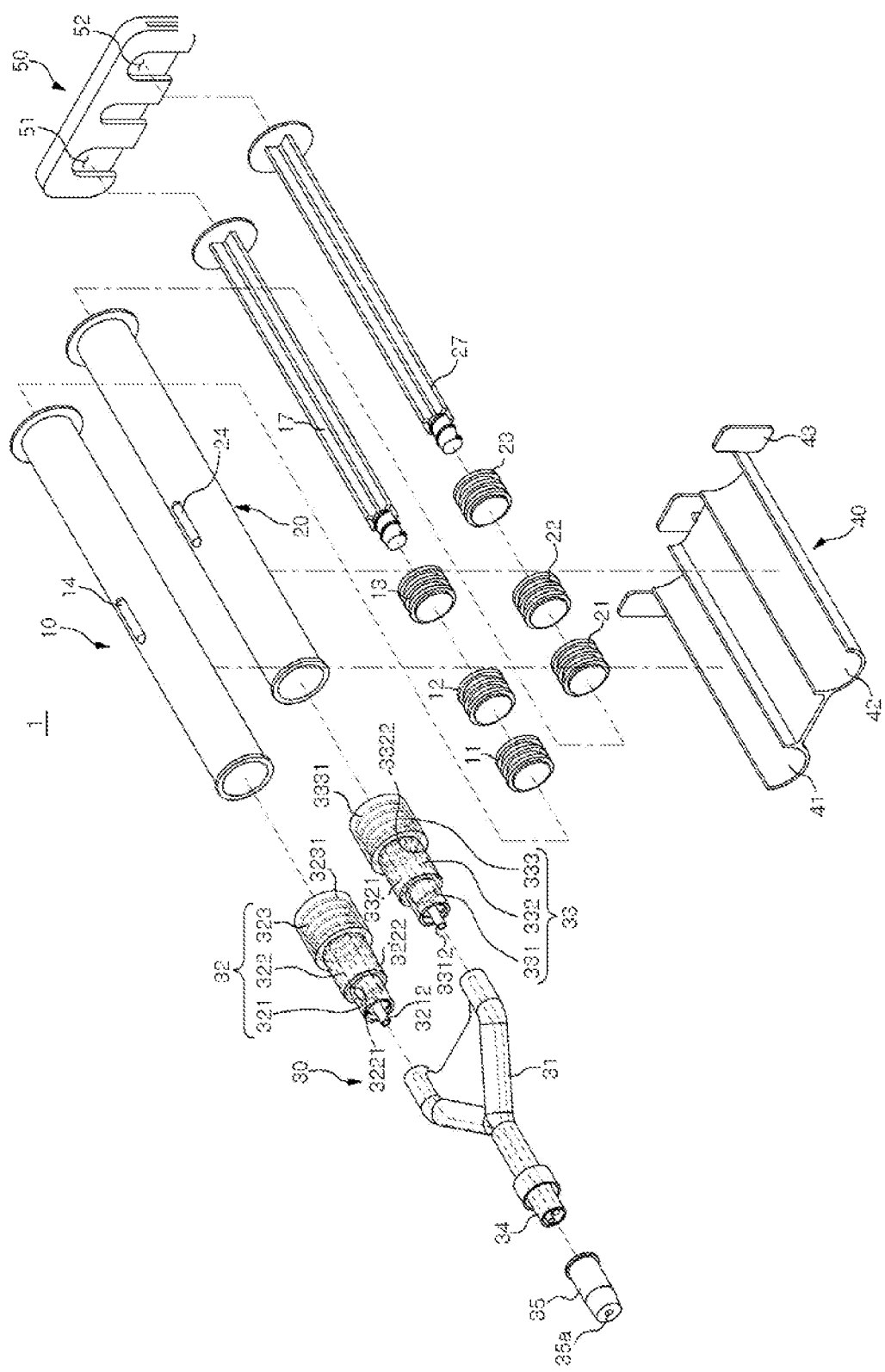
[FIG. 2]

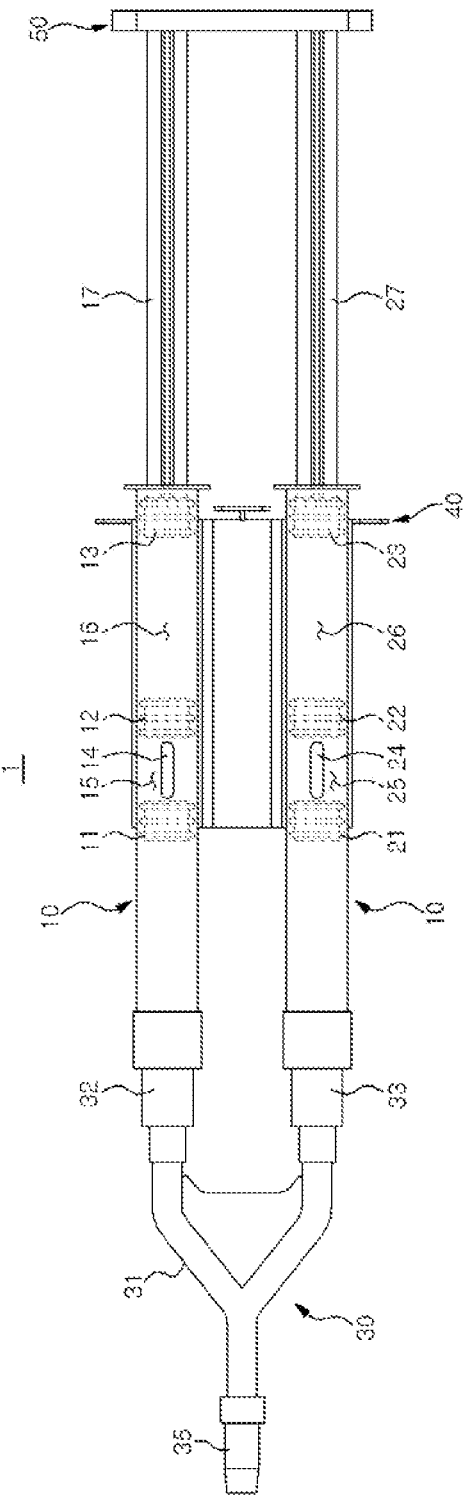
[FIG. 3]

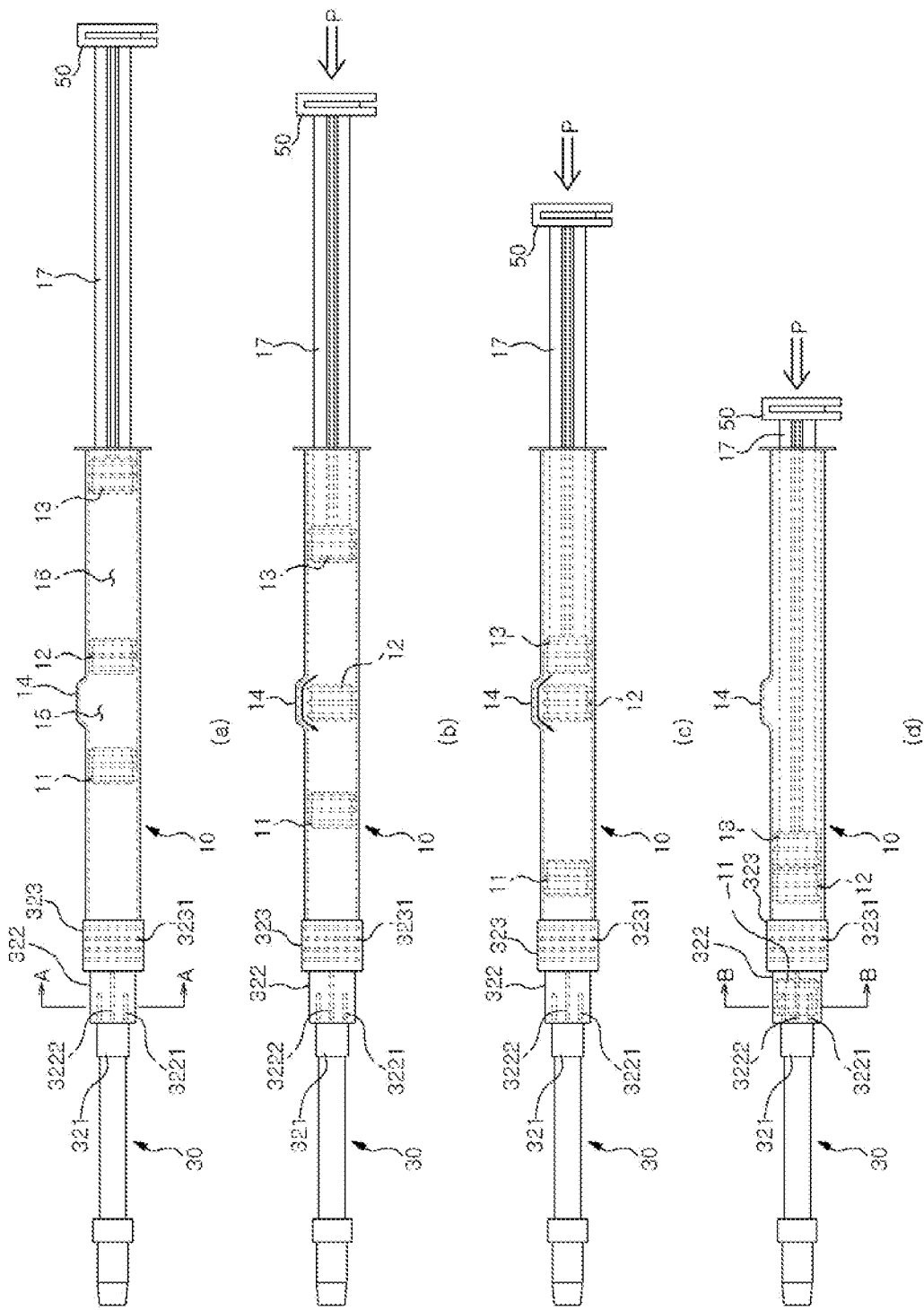
[FIG. 4]

[FIG. 5]
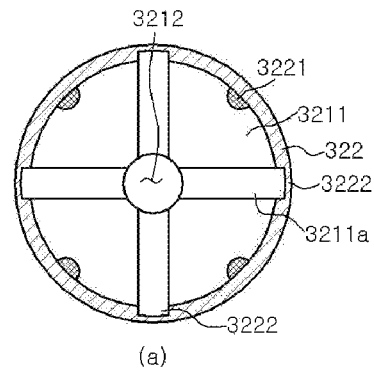
(a)
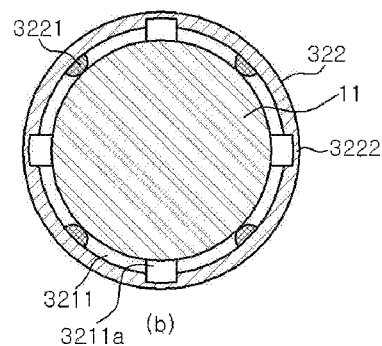
(b)
[FIG. 6]
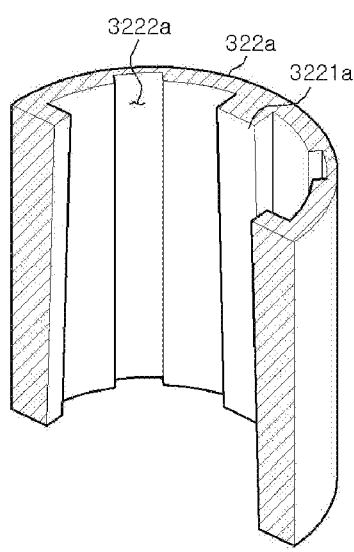

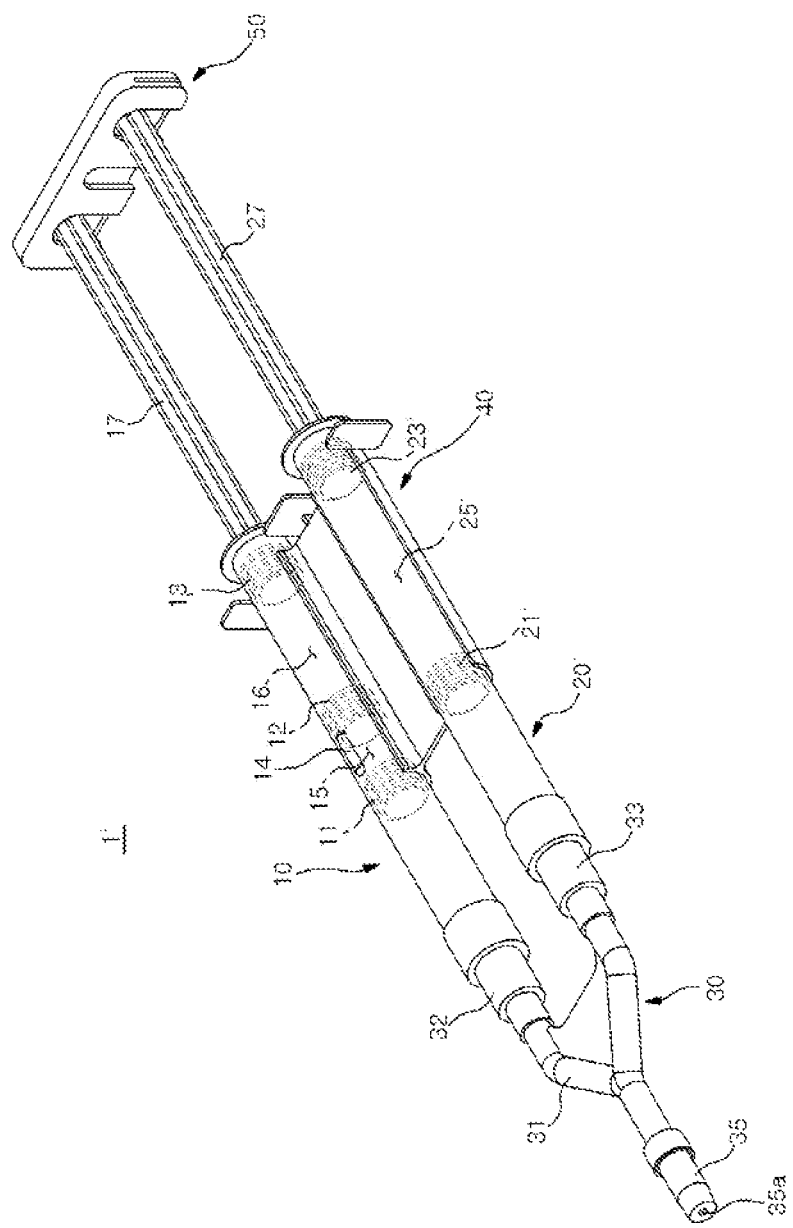

SEALANT SYRINGE ASSEMBLY

TECHNICAL FIELD

The present invention relates to a sealant syringe assembly.

BACKGROUND ART

In general, a syringe is used as one of medical supplies and can be used for various purposes such as injecting contents or collecting liquid. When the syringe is used for drug injection purposes, a user may introduce a component provided in a container, such as an ampoule or vial, into the syringe and then inject the component into a patient. With the syringe, a single component or a mixture of components can be injected. Besides, the syringe may be used for applying a sealant for adhering various living tissues to a living body.

Conventionally, a syringe and a vial containing a powder drug have been provided in the form of an assembly kit so that they could be assembled or coupled for use at a medical site. The assembly kit, however, was inconvenient to use because it required an on-site assembling or coupling task and was difficult to use promptly at a medical site because the on-site assembling or coupling task required a certain time.

A syringe pre-loaded with the powder drug and other components could be a possible solution to the problems. The powder drug, however, could be exposed to contaminated environments. Due to shaking or mishandling of the pre-loaded syringe, an unwanted reaction (e.g., a cross-linking reaction) could occur inside the syringe, which could cause the pre-loaded syringe to become unusable.

A recently proposed syringe has a plurality of chambers and is provided with powder drugs and solutions in different chambers. The powder drugs and solution, however, can be inadvertently mixed due to user's careless handling of the syringe.

Particularly, in the case of a sealant syringe which forms a sealant by mixing a plurality of solutions, solutions can be mixed at an unintended time point and a resulting sealant can block a discharge flow path, which can cause the syringe itself to become unusable.

DISCLOSURE

Technical Problem

The present invention has been made to solve the above-mentioned problems, and embodiments of the present invention provide a sealant syringe assembly capable of providing a sealant formed by mixing solutions in a single operation.

Further, embodiments of the present invention provide a sealant syringe assembly in which solutions are prevented from being mixed at an unintended time point.

Technical Solution

In accordance with an aspect of the present invention, a sealant syringe assembly is provided comprising: a first syringe including a plurality of chambers and discharging a first solution which is a mixture of a buffer solution and a compound powder; a reaction solution syringe including at least one chamber and discharging a reaction solution capable of reacting with the first solution; a base on which the first syringe and the reaction solution syringe are seated; and a connector for connecting the first syringe and the reaction solution syringe to mix and discharge the first solution and the reaction solution, wherein the first solution reacts with the reaction solution to cause change in properties such that a shear storage modulus exceeds a shear loss modulus, wherein the first syringe includes: three or more packing members provided inside the first syringe, a passage provided in an inner circumferential surface of the first syringe, and a plunger for providing pressure to one of the packing members, wherein a buffer solution is provided in one of the chambers provided between the three packing members and a compound powder is provided in another chamber, and wherein the reaction solution syringe includes: at least two packing members provided inside the reaction solution syringe, and a plunger for providing pressure to one of the packing members.

Further, the sealant syringe assembly is provided, wherein the reaction solution is a second solution which is a mixture of a buffer solution and a compound powder capable of reacting with the first solution, and the reaction solution syringe is a second syringe including a plurality of chambers, wherein the second syringe includes: three packing members provided inside the second syringe, a passage provided in the inner circumferential surface of the second syringe, and a plunger for providing pressure to one of the packing members of the second syringe, and wherein a buffer solution is provided in one of the chambers provided between the three packing members of the second syringe, and a compound powder is provided in another chamber.

Further, the sealant syringe assembly is provided, wherein the first solution is a solution in which a compound having a highly reactive functional group is dissolved, and the second solution is a solution in which a compound having a functional group capable of reacting with a compound of the first solution is dissolved.

Further, the sealant syringe assembly is provided, wherein the plurality of chambers of the second syringe are spatially connected to each other through the passage when pressure is applied to the packing members via the plunger, and the buffer solution flows through the passage and is mixed with the compound powder.

Further, the sealant syringe assembly is provided, wherein the reaction solution comprises a buffer solution, and the reaction solution syringe is a third syringe including one chamber and two packing members provided inside the third syringe, and wherein a compound powder having a lower reactivity than the first solution is contained in the other chamber of the first syringe or inside the chamber of the third syringe.

Further, the sealant syringe assembly is provided, wherein a chemical reaction occurs immediately upon mixing of the first solution and the reaction solution.

Further, the sealant syringe assembly is provided, wherein the first syringe and the reaction solution syringe comprises a first packing member and a fourth packing member disposed nearest to the connector, respectively, and wherein the first packing member and the fourth packing member respectively block movement of the first solution and the reaction solution, such that the first solution and the reaction solution can be discharged to the connector simultaneously.

Further, the sealant syringe assembly is provided, wherein the first solution and the reaction solution are moved to the connector through grooves formed on inner circumferential surfaces of respective packing member fixing portions thereof after the first packing member and the fourth packing member are respectively fitted to the packing member fixing portions.

Further, the sealant syringe assembly is provided, wherein the plurality of chambers of the first syringe are spatially connected to each other through the passage when pressure is applied to the packing member via the plunger, and the buffer solution can flow through the passage and is mixed with the compound powder.

In accordance with another aspect of the present invention, a sealant syringe assembly is provided comprising: a first syringe including a plurality of chambers and discharging a first solution which is a mixture of a buffer solution and a compound powder; a reaction solution syringe including at least one chamber and discharging a reaction solution capable of reacting with the first solution; a base on which the first syringe and the reaction solution syringe are seated; and a connector for connecting the first syringe and the reaction solution syringe to mix and discharge the first solution and the reaction solution, wherein the first solution reacts with the reaction solution to cause change in properties such that a shear storage modulus exceeds a shear loss modulus, wherein the connector includes: a connector body serving as a flow path of the first solution and the reaction solution, a first connecting portion connected to the first syringe, a second connecting portion connected to the reaction solution syringe, a connector head to which the first solution and the reaction solution are discharged, and a nozzle coupled to an end of the connector head and provided with an internal space for mixing solutions and with an injection hole, wherein each of the first connecting portion and the second connecting portion includes: a body connecting portion connected to the connector body, a syringe connecting portion connected to the first syringe or the reaction solution syringe, and a packing member fixing portion provided between the body connecting portion and the syringe connecting portion and provided with a plurality of protrusions therein, and wherein packing members are fitted to the protrusions, and the first solution or the reaction solution can move between the plurality of protrusions and can be discharged through the nozzle.

Further, the sealant syringe assembly is provided, wherein the compound powder is a synthetic polymer of any one of poly ethylene glycol (PEG), poly vinyl alcohol (PVA), and poly ethylene imine (PEI).

Further, the sealant syringe assembly is provided, wherein the compound powder is a natural polymer of any one of chitosan, hyaluronic acid, alginate, gelatin, dextran, alpha glucan, betaglucan, chondroitin sulfate and poly glutamic acid (PGA).

Further, the sealant syringe assembly is provided, wherein the buffer solution is a distilled water or an aqueous solution in which one or more of sodium chloride (NaCl), potassium chloride (KCl), monosodium phosphate (NaH2PO4), disodium phosphate (Na2HPO4), monopotassium phosphate (KH2PO4), sodium carbonate (Na2CO3), hydrochloric acid (HCl), Borate, MES, Tris, and HEPES are dissolved.

Further, the sealant syringe assembly is provided, wherein the plungers of the first syringe and the reaction solution syringe are coupled to a plunger holder, thereby making it possible to simultaneously apply pressure to the packing members of the first syringe and the reaction solution syringe.

Advantageous Effects

The sealant syringe assemblies according to embodiments of the present invention can form a sealant by mixing solutions in a single operation.

Also, the sealant syringe assemblies can prevent solutions therein from being mixed at an unintended time point.

DESCRIPTION OF DRAWINGS

FIG. 1 is a perspective view illustrating a sealant syringe assembly according to an embodiment of the present invention.

FIG. 2 is an exploded perspective view of the sealant syringe assembly of FIG. 1.

FIG. 3 is a plan view of the sealant syringe assembly of FIG. 1.

FIG. 4 is a side view of the sealant syringe assembly of FIG. 1 for explaining the operation of the sealant syringe assembly.

FIG. 5 is a cross-sectional view of the sealant syringe assembly of FIG. 1, which is taken along lines A-A and B-B in FIG. 4.

FIG. 6 is a cutaway perspective view showing another example of the first packing member fixing portion of the sealant syringe assembly of FIG. 1.

FIG. 7 is a perspective view illustrating a sealant syringe assembly according to another embodiment of the present invention.

BEST MODE

Hereinafter, some embodiments of the present invention will be explained in detail with reference to the drawings.

The detailed description for known components or functions is omitted herein when it is determined that that description would obscure essential points of the disclosure.

FIG. 1 is a perspective view of a sealant syringe assembly according to an embodiment of the present invention, FIG. 2 is an exploded perspective view thereof, FIG. 3 is a plan view thereof, FIG. 4 is a side view thereof for explaining the operation thereof; and FIG. 5 is a cross-sectional view thereof taken along lines A-A and B-B in FIG. 4.

Referring to FIGS. 1 to 5, a sealant syringe assembly 1 according to an embodiment of the present invention may comprise a first syringe 10 for discharging a first solution, a reaction solution syringe 20 which contains one or more chambers and is configured to discharge a reaction solution capable of reacting with the first solution, a connector 30 for connecting the first syringe 10 and the reaction solution syringe 20, and a base 40 on which the first syringe 10 and the reaction solution syringe 20 are seated.

In the present embodiment, a second syringe including a plurality of chambers is provided as an example of the reaction solution syringe 20. Hereinafter, for convenience of explanation, the second syringe will be denoted by reference numeral 20 in the drawings, and the reaction solution discharged from the second syringe 20 will be referred to as a second solution.

The first solution may be a solution in which a compound having a highly reactive functional group is dissolved, and the second solution may be a solution in which a compound having a functional group capable of reacting with the compound of the first solution is dissolved. The highly reactive compound of the first solution may attack the functional group of the second solution to form a chemical bond. Here, the functional group of the compound of the second solution may be less reactive than the functional group of the compound of the first solution.

Examples of a highly reactive functional group that can be used in the first solution and optionally in the second solution include an aldehyde group (—CHO), an N-hydroxysuccinimide group (—NHS), a thiol group (—SH), a vinylsulfone group (—VS), a maleimide group, an isocyanate group, an acetoacetate group or the like. Examples of a less reactive functional group that can be mainly used in the second solution include an amine group (—NH2) and a hydroxyl group (—OH). These representative compounds containing an amine group may be poly(ethylene imine) (PEI), multi armed-PEG-amine, poly(lysine), trilysine amine, poly(allylamine), and the like.

When the first solution and the second solution are mixed, the shear storage modulus exceeds the shear loss modulus. That is, the first solution and the second solution are mixed with each other to be in a hydrogel state and can be used as a sealant. Also, the reaction of the first solution with the second solution may occur immediately upon mixing. Thus, the location and timing of the mixing of the first solution and the second solution are very important for the sealant syringe assembly.

In the embodiment, the sealant is formed by the reaction of the first solution and the second solution, and it can be understood as a material that can be applied to a body of a subject to bond or join two tissues or two parts to each other.

Any compound which can change one state to another state over time in an aqueous solution or a dissolved state can be used in the embodiment of the present invention. It may be a polymer substance, a monomolecular substance, a compound of a polymer substance and a monomolecular substance, a compound of a polymer substance and another polymer substance, and the like, for example. Here, the change in the state may be understood as a case in which the reactivity of a reactive functional group existing in a compound is reduced or permanently lost in an aqueous solution or a case in which a self-reaction of a reactive functional group present in a compound occurs, causing self-crosslinking to form a hydrogel.

The first syringe 10 may be provided with a plurality of packing members 11, 12, and 13, which define a plurality of chambers 15 and 16. Specifically, the plurality of packing members 11, 12, and 13 may be provided inside the first syringe 10 at predetermined intervals. Each of the packing members 11, 12, and 13 may be provided with protrusions (not shown) at predetermined intervals. Here, the protrusions may be formed to ensure the airtightness and mobility of the packing members 11, 12, and 13 within the first syringe 10.

That is, the protrusions (not shown) of the packing members 11, 12, and 13 can be formed in a size corresponding to the inner diameter of the first syringe 10, thereby enabling the inside of the syringe 10 to be kept in a closed state.

As illustrated as the embodiment, the first packing member 11 is provided at a position closest to the connector 30, and the second packing member 12 and the third packing member 13 are provided in this order at predetermined intervals. The space between the first packing member 11 and the second packing member 12 is the first chamber 15, the space between the second packing member 12 and the third packing member 13 is the second chamber 16, and an empty space is provided in the front end of the first packing member 11. The configuration of the plurality of packing members 11, 12, and 13 and the chambers 15 and 16 is not limited to the illustrated configuration, however. For example, the syringe assembly may have four packing members and three chambers defined by the four packing members.

The first chamber 15 may be a space in which a compound powder that is a solid material is provided. At this time, the compound powder filled in the first chamber 15 can be isolated from the empty space located at the front end of the first packing member 11 by the first packing member 11.

The first packing member 11 and a fourth packing member 21, which is described below, may play the role of preventing the first solution to be mixed in the first chamber 15 and the second solution to be mixed in the third chamber 25 from being discharged at an unwanted time point. That is, the discharging of the first solution from the first syringe 10 and the discharging of the second solution from the second syringe 20 are synchronized by the first packing member 11 and the fourth packing member 21.

The compound powder may be provided as a synthetic polymer of any one of PEG (poly ethylene glycol), PVA (poly vinyl alcohol) and PEI (poly ethylene imine), but the compound powder provided in the first chamber 15 is not limited thereto. For example, it may be a natural polymer of any one of chitosan, hyaluronic acid, alginate, gelatin, dextran, alpha glucan, beta glucan, chondroitin sulfate and poly glutamic acid, or it may be a compound capable of reacting with another compound to form a sealant.

The second chamber 16, which is separated from the first chamber 15 by the second packing member 12, may be a space in which a liquid that can dissolve a compound powder (i.e., a buffer solution) is provided. Specifically, the second packing member 12 provided with one or more protrusions (not shown) can seal a predetermined space inside the first syringe 10 and prevent the buffer solution of the second chamber 16 from flowing into the inside of the first chamber 15. The buffer solution may be an aqueous solution in which sodium chloride (NaCl), potassium chloride (KCl), monosodium phosphate (NaH2PO4), disodium phosphate (Na2HPO4), monopotassium phosphate (KH2PO4), sodium carbonate (Na2CO3), hydrochloric acid (HCl), borate, MES, Tris, HEPES, or any combination thereof is dissolved, but it is not limited thereto. For example, it may be distilled water.

The third packing member 13 can be moved by pressure generated by a first plunger 17. Specifically, the pressure may be generated by user's fingers.

An end of the first plunger 17 is in contact with the third packing member 13 in the first syringe 10, and the other end of the first plunger 17 is exposed to the outside of the first syringe 10. When a user pushes the other end of the first plunger 17, a force generated by the user can be transmitted to the third packing member 13. As the diameter of the first plunger 17 is smaller than the inner diameter of the first syringe 10, the first plunger 17 can be easily moved inside the first syringe 10.

The first syringe 10 may comprise a first passage 14 serving as a bypass for fluid flow. The first passage 14 is formed as a groove that extends longitudinally on the inner circumferential surface of the first syringe 10 so as to provide a space for fluid flow in the wall of the first syringe 10.

The first passage 14 may be integrally formed with the first syringe 10 made of glass material. The outer side of the first passage 14 may protrude relative to the outer circumferential surface of the first syringe 10 at a predetermined position. The length of the first passage 14 may be identical or similar to the length of the packing member 11, 12, or 13. The first passage 14 may be provided between the first packing member 11 and the second packing member 12. The specific role of the first passage 14 will be described below.

A second syringe 20 may be provided at a predetermined interval from the first syringe 10. The shape of the second syringe 20 may be identical to that of the first syringe 10.

That is, the second syringe 20 may include fourth, fifth and sixth packing members 21, 22, and 23, a second passage 24, third and fourth chambers 25 and 26, and a second plunger 27 that have the same or similar shapes and roles of the first, the second and third packing members 11, 12 and 13, the first passage 14, the first and second chambers 15 and 16, and the first plunger 17 of the first syringe 10 described above. However, the shape of the second syringe 20 is not limited that of the first syringe 10. For example, the second syringe 20 may be formed to have a diameter less than that of the first syringe 10, and the diameters of the fourth, fifth and sixth packing members 21, 22, and 23, the second passage 24, the third and fourth chambers 25 and 26, and the second plunger 27 may be adjusted accordingly.

The first syringe 10 and the second syringe 20 can be connected through the connector 30.

For example, the inner space of the first syringe 10 and the inner space of the second syringe 20 may be connected to the inner space of the connector 30, and then connected to each other in the inner space of a nozzle 35.

The inner space of the nozzle 35 coupled to the connector 30 may be a space where the first solution supplied from the first syringe 10 and the second solution supplied from the second syringe 20 are mixed with each other to perform a chemical reaction. Although it is described in this embodiment that the first solution and the second solution are mixed in the nozzle 35 and then discharged, the first solution and the second solution may be mixed in the inner space of the connector 30 in other embodiments.

The connector 30 may be provided with a connector body 31, a first connecting portion 32 connected to the first syringe 10, a second connecting portion 33 connected to the second syringe 20, a connector head 34 to which the first solution and the second solution are respectively discharged, and the nozzle 35 coupled to an end of the connector head 34 and provided with an injection hole 35a for injecting mixed solution. The injection hole 35a is formed at an end of the nozzle 35 and can communicate with the inner space of the nozzle 35.

The connector body 31 may function as flow paths of a plurality of solutions, that is, a first solution and a second solution.

To this end, an end of the connector body 31 may be connected to the first syringe 10 through the first connecting part 32, and another end thereof may be connected to the second syringe 20 through the second connecting part 33 so that the first solution and the second solution transferred through the first connection part 32 and the second connection part 33 can flow into the inner space of the nozzle 35 through the connector head 34. The first solution and the second solution reaching the inner space of the nozzle 35 may meet each other to form a mixed solution. At this time, a chemical reaction (for example, a crosslinking reaction) may be started. The mixed solution in the inner space of the nozzle 35 may be discharged or injected to the outside of the nozzle 35 through the injection hole 35a of the nozzle 35. The injected mixed solution can be rapidly gelated and form a hydrogel.

The first connecting portion 32 and the second connecting portion 33 connect the first syringe 10 and the second syringe 20 to the connector body 31, and the first and second connecting portions 32 and 33 may function as flow paths for the first solution and the second solution.

Specifically, the first connecting portion 32 may comprise a first body connecting portion 321 connected to an end of the connector body 31, a first syringe connecting portion 323 connected to the first syringe 10, and a first packing member fixing portion 322 provided between the first body connecting portion 321 and the first syringe connecting portion 323.

The second connecting portion 33 may comprise a second body connecting portion 331 connected to another end of the connector body 31, a second syringe connecting portion 333 connected to the second syringe 20, and a second packing member fixing portion 332 provided between the body connecting portion 331 and the second syringe connecting portion 333.

The first body connecting portion 321 and the second body connecting portion 331 may be provided with a threaded portion (not shown) therein, with which they can be coupled to the connector body 31. However, the method of coupling the first body connecting portion 321 and the second body connecting portion 331 with the connector body 31 is not limited to the-above described method, and the first and second body connection portions may be coupled to the connector body 31 through a separate coupling member, for example.

The inner spaces of the first body connecting portion 321 and the first packing member fixing portion 322 are connected to each other, and the inner spaces of the second body connecting portion 331 and the second packing member fixing portion 332 are connected to each other.

Here, the first packing member fixing portion 322 and the second packing member fixing portion 332 may fix or stop the first packing member 11 and the fourth packing member 21 that are supposed to move according to fluid pressure.

To this end, the first packing member fixing portion 322 and the second packing member fixing portion 332 may be provided with first protrusions 3221 and second protrusions 3321 that correspond to the diameters of the first packing member 11 and the fourth packing member 21. A first blocking portion 3211 may be provided between the first body connecting portion 321 and the first packing member fixing portion 322, and a second blocking portion 3311 may be provided between the second body connecting portion 331 and the second packing member fixing portion 332. The specific structure of the first packing member fixing portion 322 and the second packing member fixing portion 332 will be described below.

The connector 30 may be connected to the first syringe 10 and the second syringe 20 through the first syringe connecting portion 323 and the second syringe connecting portion 333. The first syringe connecting portion 323 and the second syringe connecting portion 333 may be provided with a plurality of grooves 3231 and 3331 therein, and an end of the first syringe 10 and an end of the second syringe 20 may have a diameter that is larger than those of the first and second syringe connecting portions 323 and 333 but smaller than those of the grooves 3231 and 3331.

Specifically, in order to couple the first syringe 10 and the second syringe 20 with the connector 30, heat may be applied to the first syringe connecting portion 323 and the second syringe connecting portion 333. The first syringe connecting portion 323 and the second syringe connecting portion 333 may be formed of a thermoplastic material (e.g., polypropylene (PP)) that can be deformed upon application of heat. When heat is applied to the first syringe connecting portion 323 and the second syringe connecting portion 333, a polymer that has been cured is softened and the ends of the first syringe 10 and the second syringe 20 can be inserted into the grooves 3231 and 3331 of the first syringe connecting portion 323 and the second syringe connecting portion 333. When the first syringe connecting portion 323 and the second syringe connecting portion 333 are cured again after a predetermined time has passed, the first syringe connecting portion 323 and the second syringe connecting portion 333 may be fixed while being inserted into the grooves 3231 and 3331. As a result, the first syringe connecting portion 323 and the second syringe connecting portion 333 can be easily coupled with the first syringe 10 and the second syringe 20.

On the other hand, the first syringe 10 and the second syringe 20 can be seated on the base 40. The base 40 is provided for fixing the first syringe 10 and the second syringe 20, and it may comprise a first seating portion 41 on which the first syringe 10 is seated, a second seating portion 42 on which the second syringe 20 is seated, and a wing-shaped support 43 protruding outwardly of the first and second seating portions 41 and 42. Here, the support 43 can play a role of supporting the pressure of user's fingers so that the plungers 17 and 27 can be moved through a plunger holder 50.

The first seating portion 41 and the second seating portion 42 may be shaped to correspond to the diameters of the first syringe 10 and the second syringe 20, and the support 43 may be provided on one side of the first seating portion 41 and the second seating portion 42 to be positioned at a storage position.

The first plunger 17 and the second plunger 27 of the first syringe 10 and the second syringe 20 may be coupled via the plunger holder 50. Specifically, the other ends of the first plunger 17 and the second plunger 27, which are exposed to the outside of the first syringe 10 and the second syringe 20, may be coupled to the first coupling portion 51 and the second coupling portion 52 of the plunger holder 50, respectively. A part of the first coupling portion 51 and a part of the second coupling portion 52 can be opened to a size larger than the diameters of the first plunger 17 and the second plunger 27, and along this open space, the first plunger 17 and the second plunger 27 can be fit-coupled together. As a result, a user can press the first plunger 17 and the second plunger 27 simultaneously by applying pressure to the plunger holder 50.

Referring to FIG. 4(a), the first chamber 15 may be provided with a compound powder, and the second chamber 16 may be provided with a buffer solution. Although, FIG. 4 illustrates a side view of only the first syringe 10, the operation of the second syringe 20 is substantially the same as that of the first syringe 10.

When a user applies pressure to the plunger holder 50, the first plunger 17 can push the third packing member 13. As a result, the third packing member 13 can push the buffer solution provided in the second chamber 16, and the second packing member 12 can be moved by the moving length of the third packing member 13. That is, the volume of the second chamber 16 may be unchanged.

Due to the pressure by the first plunger 17, the second packing member 12 can be moved to a position corresponding to the first passage 14, as shown in FIG. 4(b). The first chamber 15 and the second chamber 16 can be in fluid communication with each other by the first passage 14.

As a result, the buffer solution in the second chamber 16, which has been partitioned from the first chamber 15 by the second packing member 12, can be moved to the first chamber 15 through the first passage 14. Thus, while the volume of the second chamber 16 between the second packing member 12 and the third packing member 13 can be gradually decreased, the volume of the first chamber 15 can be gradually increased. When all of the buffer solution in the second chamber 16 is moved to the first chamber 15, the buffer solution can be mixed with the compound in the first chamber 15, as shown in FIG. 4(c). The solution mixed in the first chamber 15 is referred to as the first solution. That is, the first solution may be a mixture of a solid compound powder and a liquid buffer solution.

Once all of the buffer solution in the second chamber 16 is moved, the second packing member 12 and the third packing member 13 can be moved while they are in close contact with each other. Along with the movement of the second packing member 12 and the third packing member 13, the first solution in the first chamber 15 can be moved such that the first packing member 11 can be moved to the inside of the first packing member fixing portion 322 of the connector 30, as shown in FIG. 4(d).

The first packing member 11 can be fit-coupled to the protrusions 3221 of the first packing member fixing portion 322, and the first solution inside the first chamber 15 is introduced to the inner circumferential surface of the first packing member fixing portion 322 and then can be passed through spaces between the protrusions 3221 spaced apart from each other. Grooves 3222, each of which is positioned between two of the protrusions 3221, may be provided in the inner surface of the first packing member fixing portion 322, thereby allowing the first solution to flow also through the grooves 3222.

Meanwhile, a through hole 3212 may be provided at a side of the first body connecting portion 321, and a first blocking portion 3211 may be provided between the first body connecting portion 321 and the first packing member fixing portion 322. The first blocking portion 3211 may be provided with a connecting groove 3211a extending from the grooves 3222 to the through hole 3212. That is, the grooves 3222 of the first packing member fixing portion 322 and the connecting groove 3211a of the first blocking portion 3211 can be connected to each other. Therefore, the first solution moving along the grooves 3222 can be moved to the through hole 3212 via the connecting groove 3211a. The first solution discharged through the through hole 3212 may be moved to the connector head 34 through the connector body 31 of the connector 30 and then discharged or injected through the injection hole 35a of the nozzle 35.

A substantially identical pressure is applied to the first syringe 10 and the second syringe 20 through the plunger holder 50, and the second solution can be discharged in the same process as the first solution is discharged.

The first solution and the second solution from the first syringe 10 and the second syringe 20 can be simultaneously discharged to the connector 30 by the operation of a user and then can be mixed at the nozzle 35 just before spraying.

In the prior art, there were problems that solutions discharged from syringes are mixed too early or too late, or they are mixed at unintended positions. However, according to the present invention, the first packing member 11 and the fourth packing member 21 prevent the first solution and the second solution from being discharged. After the first packing member 11 and the fourth packing member 21 are inserted to the first packing member fixing portion 322 and the second packing member fixing portion 332 at substantially the same time point, the first and second solutions can be discharged toward the connector 30. Accordingly, a problem that flow path may be clogged due to mixing of the first solution and the second solution at unwanted positions can be prevented.

That is, the discharge of the first solution from the first syringe 10 and the discharge of the second solution from the second syringe 20 are synchronized by the movement of the first packing member 11 and the fourth packing member 21, and the positions of the respective packing members and the volumes of the chambers can be set such that the first packing member 11 and the fourth packing member 21 are simultaneously inserted into the first packing member fixing portion 322 and the second packing member fixing portion 332.

In addition, the first and second solutions are not mixed within the connector 30 but mixed and injected at the nozzle 35 immediately before discharge, thereby preventing the first and second solutions from being mixed at an unintended time point. In addition, the first syringe 10 and the second syringe 20 are injected at the same time, thereby enabling the first and second solutions to be mixed in a single operation.

Also, in case of conventional products, because a step of mixing a plurality of solutions or a step of mounting a syringe to an applicator has to be performed separately from and immediately before a step of injecting the mixed solutions, it takes a lot of time to inject the solutions, thereby resulting in inconvenience to users and the solutions could be exposed to external air during the on-site preparation task, thereby causing a risk of contamination of the solutions. In contrast, in case of an assembled syringe product, according to the embodiments of the present invention, the assembled syringe can be used at a medical site immediately after removing only a sterile package from the assembled syringe product.

FIG. 6 is a cutaway perspective view showing another example of the first packing member fixing portion of the sealant syringe assembly of FIG. 1.

Referring to FIG. 6, the first syringe 10 may comprise a first packing member fixing portion 322a having another type of protrusions 3221a. The protrusions 3221a of the first packing member fixing portion 322a may be provided to have a rectangular cross section and may be provided so that the size gradually increases as they go towards the solution discharging position. The first packing member fixing portion 322a may have a tapered structure. Specifically, the inner diameter of the first syringe 10 formed through the protrusions 3221a may become smaller towards the side from which the solution is discharged, and accordingly, the first packing member 11 can be more firmly fixed as it is more deeply inserted into the first packing member fixing portion 322a. Grooves 3222a, each of which is positioned between two of the protrusions 3221a, may be provided in the inner surface of the first packing member fixing portion 322a, thereby allowing the first solution to flow also through the grooves 3222a.

Hereinafter, a sealant syringe assembly according to another embodiment of the present invention will be described with reference to FIG. 7. In the another embodiment, the second syringe 20 of the embodiment of FIG. 1 is replaced with a third syringe 21'. The third syringe 21' includes a fourth packing member 21', a sixth packing member 23', and a fifth chamber 25' defined between the fourth and sixth packing members 21' and 23'. The difference between the embodiments will be mainly described below, and descriptions and reference numerals of the embodiment of FIG. 1 are used for the same elements.

FIG. 7 is a perspective view illustrating a sealant syringe assembly according to another embodiment of the present invention.

Referring to FIG. 7, a sealant syringe assembly 1' according to another embodiment of the present invention comprises a third syringe having one chamber as a reaction solution syringe 20'. Hereinafter, for convenience of explanation, the third syringe will be referred to as a reference numeral 20', and the reaction solution discharged from the third syringe 20' will be referred to as a third solution.

The third syringe 20' may comprise the fourth packing member 21' and the sixth packing member 23', and the fifth chamber 25' may be provided between the fourth packing member 21' and the sixth packing member 23'.

The fifth chamber 25' is provided with the third solution that is either a buffer solution that can react with the first solution or a buffer solution in which a compound powder capable of reacting with the compound powder contained in the first solution is dissolved.

In case where a buffer solution that can react with the first solution is provided in the fifth chamber 25', the first chamber 15 of the first syringe 10 is filled with a mixture of a highly reactive compound powder and a relatively less reactive compound powder that can react with the highly reactive compound powder may be provided. This mixture is mixed with the buffer solution provided in the second chamber 16 of the first syringe 10 and discharged and may be reacted with the buffer solution provided from the third syringe 20'.

In case where a buffer solution containing a compound powder capable of reacting with the compound powder contained in the first solution is provided in the fifth chamber 25', the compound powder provided in the fifth chamber 25' may be a compound powder which is relatively less reactive than the compound powder provided in the first syringe 10. The first solution containing the compound powder having a high reactivity and the third solution containing the compound powder having a low reactivity are discharged from the first syringe 10 and the third syringe 20' respectively, become in contact with each other, and reacted with each other.

When the third syringe 20' receives pressure through the plunger 27, the third solution may be discharged to the connector 30 and mixed with the first solution.

The discharge of the first solution from the first syringe 10 and the discharge of the second solution from the third syringe 20' may be synchronized by the movement of the first packing member 11 and the fourth packing member 21', and the positions of the respective packing members and the volumes of the chambers can be set such that the first packing member 11 and the fourth packing member 21' are simultaneously inserted into the first packing member fixing portion 322 and the second packing member fixing portion 332, respectively. For example, the inner diameter of the third syringe 20' may be adjusted to match the speed of the first solution and the third solution. Thus, the first solution and the third solution can be mixed simultaneously in the connector 30.

While the sealant syringe assemblies according to embodiments of the present invention are described as specific embodiments, these are merely exemplary embodiments, and the present invention should be construed in a broadest scope based on the fundamental ideas disclosed herein, rather than being limited to them. By combining or replacing a part or parts of embodiments disclosed herein, ordinary skilled in the art may carry out a type of form which is not explicitly described herein, and it should be noted that it is not depart from the scope of the present invention. Besides, ordinary skilled in the art may easily change or modify embodiments disclosed herein based on the disclosure, and it is obvious that such change or modification also falls within the scope of the present invention.

INDUSTRIAL APPLICABILITY

The present invention is applicable in the medical device industry.

The invention claimed is:

1. A sealant syringe assembly comprising:
    a first syringe for discharging a first solution;
    a reaction solution syringe for discharging a reaction solution capable of reacting with the first solution;
    a base on which the first syringe and the reaction solution syringe are seated; and
    a connector for connecting the first syringe and the reaction solution syringe to mix and discharge the first solution and the reaction solution,
    wherein the first solution reacts with the reaction solution to cause change in properties such that a shear storage modulus exceeds a shear loss modulus,
    wherein the first syringe includes:
        three or more packing members provided inside the first syringe;
        chambers defined by adjacent packing members of the three or more packing members, wherein a first buffer solution is provided in one of the chambers, and a first compound powder is provided in another chamber;
        a first passage provided in an inner circumferential surface of the first syringe; and
        a first plunger for providing pressure to one of the three or more packing members,
    wherein the reaction solution syringe includes:
        at least two packing members provided inside the reaction solution syringe; and
        at least one chamber defined by adjacent packing members of the at least two packing members,
    wherein the first syringe comprises a first packing member, which is included in the three or more packing members, disposed near the connector, and the reaction solution syringe comprises a fourth packing member, which is included in the at least two packing members, disposed near the connector,
    wherein the connector includes a first packing member fixing portion and a second packing member fixing portion, and
    wherein after the first packing member and the fourth packing member are fitted to the first packing member fixing portion and the second packing member fixing portion, respectively, the first solution and the reaction solution are moved to the connector through grooves formed on inner circumferential surfaces of the first packing member fixing portion and the second packing member fixing portion, respectively.

2. The sealant syringe assembly according to claim 1, wherein the reaction solution syringe includes:
    three packing members, which are included in the at least two packing members, provided inside the reaction solution syringe;
    chambers, which are included in the at least one chamber, defined between adjacent packing members of the three packing members;
    a second passage provided in an inner circumferential surface of the reaction solution syringe; and
    a second plunger for providing pressure to one of the three packing members of the reaction solution syringe, and
    wherein a second buffer solution is provided in one of the chambers of the reaction solution syringe, and a second compound powder is provided in the other chamber.

3. The sealant syringe assembly according to claim 2, wherein the first compound powder provided in the first syringe has a functional group with a high reactivity, and the second compound powder provided in the reaction solution syringe has a functional group capable of reacting with the functional group of the first compound provide in the first syringe.

4. The sealant syringe assembly according to claim 2, wherein when pressure is applied to at least one of the packing members of the reaction solution syringe via the second plunger, the chambers of the reaction solution syringe become in fluid communication with each other through the second passage, thereby allowing the second buffer solution in one of the chambers of the reaction solution syringe to flow, through the second passage, to another chamber of the chambers of the reaction solution syringe where the second compound powder in the another chamber of the chambers of the reaction solution syringe is mixed with the second buffer solution.

5. The sealant syringe assembly according to claim 1, wherein a chemical reaction occurs immediately upon mixing of the first solution and the reaction solution.

6. The sealant syringe assembly according to claim 1, wherein when pressure is applied to at least one of the packing members of the first syringe via the first plunger, the chambers of the first syringe become in fluid communication with each other through the first passage of the first syringe, thereby allowing the first buffer solution in one of the chambers of the first syringe to flow, through the first passage, to the another chamber of the chambers of the first syringe where the first compound powder in the another chamber of the chambers of the first syringe is mixed with the first buffer solution.

7. The sealant syringe assembly according to claim 1, wherein the first compound powder is a synthetic polymer of any one of poly ethylene glycol (PEG), poly vinyl alcohol (PVA), and poly ethylene imine (PEI).

8. The sealant syringe assembly according to claim 1, wherein the first compound powder is a natural polymer of any one of chitosan, hyaluronic acid, alginate, gelatin, dextran, alpha glucan, betaglucan, chondroitin sulfate and poly glutamic acid (PGA).

9. The sealant syringe assembly according to claim 1, wherein the first buffer solution is a distilled water or an aqueous solution in which one or more of sodium chloride (NaCl), potassium chloride (KCl), monosodium phosphate (NaH2PO4), disodium phosphate (Na2HPO4), monopotassium phosphate (KH2PO4), sodium carbonate (Na2CO3), hydrochloric acid (HCl), Borate, MES, Tris, and HEPES are dissolved.

10. The sealant syringe assembly according to claim 1, wherein the first plunger of the first syringe and a second plunger of the reaction solution syringe are coupled to a plunger holder, thereby simultaneously applying pressure to the packing members of the first syringe and the reaction solution syringe.

11. A sealant syringe assembly comprising:
    a first syringe for discharging a first solution;
    a reaction solution syringe for discharging a reaction solution capable of reacting with the first solution;
    a base on which the first syringe and the reaction solution syringe are seated; and
    a connector for connecting the first syringe and the reaction solution syringe to mix and discharge the first solution and the reaction solution,
    wherein the first solution reacts with the reaction solution to cause change in properties such that a shear storage modulus exceeds a shear loss modulus,
    wherein the first syringe includes:
        three or more packing members provided inside the first syringe;

chambers defined by adjacent packing members of the three or more packing members, wherein a first buffer solution is provided in one of the chambers, and a first compound powder is provided in another chamber;
a first passage provided in an inner circumferential surface of the first syringe; and
a first plunger for providing pressure to one of the three or more packing members,
wherein the reaction solution syringe includes:
at least two packing members provided inside the reaction solution syringe;
at least one chamber defined by adjacent packing members of the at least two packing members,
wherein the reaction solution syringe includes two packing members, which are included in the at least two packing members, and a chamber, which is included in the at least one chamber, defined between the two packing members,
wherein (i) the chamber of the reaction solution syringe contains only a second buffer solution while the another chamber of the first syringe further contains a second compound powder, or (ii) the chamber of the reaction solution syringe contains the second compound powder dissolved in the second buffer solution, and
wherein the reactivity of the first compound is higher than that of the second compound powder.

12. A sealant syringe assembly comprising:
a first syringe including a plurality of packing members and a plurality of chambers and discharging a first solution which is a mixture of a buffer solution and a first compound powder;
a reaction solution syringe including a plurality of packing members and at least one chamber and discharging a reaction solution capable of reacting with the first solution;
a base on which the first syringe and the reaction solution syringe are seated; and
a connector for connecting the first syringe and the reaction solution syringe to mix and discharge the first solution and the reaction solution,
wherein the first solution reacts with the reaction solution to cause change in properties such that a shear storage modulus exceeds a shear loss modulus,
wherein the connector includes:
a connector body serving as a flow path of the first solution and the reaction solution,
a first connecting portion connected to the first syringe,
a second connecting portion connected to the reaction solution syringe,
a connector head to which the first solution and the reaction solution are discharged, and
a nozzle coupled to an end of the connector head, the nozzle being provided with an internal space for mixing the first solution and the reaction solution and an injection hole,
wherein each of the first connecting portion and the second connecting portion includes:
a body connecting portion connected to the connector body,
a syringe connecting portion connected to the first syringe or the reaction solution syringe, and
a packing member fixing portion provided between the body connecting portion and the syringe connecting portion and provided with a plurality of protrusions therein, and
wherein one of the plurality of packing members of the first syringe and one of the plurality of packing members of the reaction syringe are fitted to the protrusions, respectively, and the first solution or the reaction solution can move between the plurality of protrusions and be discharged through the nozzle.

13. The sealant syringe assembly according to claim 12, wherein the first compound powder is a synthetic polymer of any one of poly ethylene glycol (PEG), poly vinyl alcohol (PVA), and poly ethylene imine (PEI).

14. The sealant syringe assembly according to claim 12, wherein the first compound powder is a natural polymer of any one of chitosan, hyaluronic acid, alginate, gelatin, dextran, alpha glucan, betaglucan, chondroitin sulfate and poly glutamic acid (PGA).

15. The sealant syringe assembly according to claim 12, wherein the buffer solution is a distilled water or an aqueous solution in which one or more of sodium chloride (NaCl), potassium chloride (KCl), monosodium phosphate (NaH2PO4), disodium phosphate (Na2HPO4), monopotassium phosphate (KH2PO4), sodium carbonate (Na2CO3), hydrochloric acid (HCl), Borate, MES, Tris, and HEPES are dissolved.

* * * * *